United States Patent
Serrano et al.

(10) Patent No.: US 6,478,027 B1
(45) Date of Patent: Nov. 12, 2002

(54) CONDOM DEVICE

(76) Inventors: Salvador V. Serrano, 400 Hyde St., Salinas, CA (US) 93907; Melissa M. Montes, 400 Hyde St., Salinas, CA (US) 93907

( * ) Notice: Subject to any disclaimer, the term of this patent is extended or adjusted under 35 U.S.C. 154(b) by 0 days.

(21) Appl. No.: 09/844,373

(22) Filed: Apr. 27, 2001

(51) Int. Cl.[7] .................................................. A61F 6/04
(52) U.S. Cl. .................................... 128/844; 128/918
(58) Field of Search .............................. 128/842, 844, 128/918; 604/347–353

(56) References Cited

U.S. PATENT DOCUMENTS

| | | | |
|---|---|---|---|
| 5,111,831 A | * | 5/1992 | Foggia ........................ 128/842 |
| 5,314,447 A | * | 5/1994 | Papurt ........................ 128/844 |
| 5,318,042 A | * | 6/1994 | Gray ........................... 128/844 |
| 5,718,236 A | * | 2/1998 | Curcio ........................ 128/844 |
| 6,209,543 B1 | * | 4/2001 | Star ............................ 128/844 |

* cited by examiner

*Primary Examiner*—Michael A. Brown

(57) ABSTRACT

A condom device for desensitizing the penis. The condom device includes a single and continuous sheath of thin walled tubular construction having an open first end and a closed second end. The sheath includes a pouch portion abutting the first end and a cylindrical portion abutting the second end. When the device is positioned over male genitalia the cylindrical portion covers the penis and the pouch encloses the scrotum and the base of the penis. A first elastic band extends around and is attached to the sheath. The first elastic band is positioned at a juncture of the pouch portion and the cylindrical portion. Blood flow through the penis is restricted by the first elastic band.

1 Claim, 1 Drawing Sheet

CONDOM DEVICE

BACKGROUND OF THE INVENTION

1. Field of the Invention

The present invention relates to condoms and more particularly pertains to a new condom device for desensitizing the penis.

2. Description of the Prior Art

The use of condoms is known in the prior art. More specifically, condoms heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,314,447; U.S. Pat. No. 5,111,831; U.S. Pat. No. 5,370,131; U.S. Pat. No. 362,302; U.S. Pat. No. 4,354,494; and U.S. Pat. No. 5,666,971.

While these devices fulfill their respective, particular objectives and requirements, the aforementioned patents do not disclose a new condom device. The inventive device includes a single and continuous sheath of thin walled tubular construction having an open first end and a closed second end. The sheath includes a pouch portion abutting the first end and a cylindrical portion abutting the second end. When the device is positioned over male genitalia the cylindrical portion covers the penis and the pouch encloses the scrotum and the base of the penis. A first elastic band extends around and is attached to the sheath. The first elastic band is positioned at a juncture of the pouch portion and the cylindrical portion. Blood flow through the penis is restricted by the first elastic band.

In these respects, the condom device according to the present invention substantially departs from the conventional concepts and designs of the prior art, and in so doing provides an apparatus primarily developed for the purpose of desensitizing the penis.

SUMMARY OF THE INVENTION

In view of the foregoing disadvantages inherent in the known types of condoms now present in the prior art, the present invention provides a new condom device construction wherein the same can be utilized for desensitizing the penis.

The general purpose of the present invention, which will be described subsequently in greater detail, is to provide a new condom device apparatus and method which has many of the advantages of the condoms mentioned heretofore and many novel features that result in a new condom device which is not anticipated, rendered obvious, suggested, or even implied by any of the prior art condoms, either alone or in any combination thereof.

To attain this, the present invention generally comprises a single and continuous sheath of thin walled tubular construction having an open first end and a closed second end. The sheath includes a pouch portion abutting the first end and a cylindrical portion abutting the second end. When the device is positioned over male genitalia the cylindrical portion covers the penis and the pouch encloses the scrotum and the base of the penis. A first elastic band extends around and is attached to the sheath. The first elastic band is positioned at a juncture of the pouch portion and the cylindrical portion. Blood flow through the penis is restricted by the first elastic band.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new condom device apparatus and method which has many of the advantages of the condoms mentioned heretofore and many novel features that result in a new condom device which is not anticipated, rendered obvious, suggested, or even implied by any of the prior art condoms, either alone or in any combination thereof.

It is another object of the present invention to provide a new condom device which may be easily and efficiently manufactured and marketed.

It is a further object of the present invention to provide a new condom device which is of a durable and reliable construction.

An even further object of the present invention is to provide a new condom device which is susceptible of a low cost of manufacture with regard to both materials and labor, and which accordingly is then susceptible of low prices of sale to the consuming public, thereby making such condom device economically available to the buying public.

Still yet another object of the present invention is to provide a new condom device which provides in the apparatuses and methods of the prior art some of the advantages thereof, while simultaneously overcoming some of the disadvantages normally associated therewith.

Still another object of the present invention is to provide a new condom device for desensitizing the penis.

Yet another object of the present invention is to provide a new condom device which includes a single and continuous sheath of thin walled tubular construction having an open first end and a closed second end. The sheath includes a pouch portion abutting the first end and a cylindrical portion abutting the second end. When the device is positioned over male genitalia the cylindrical portion covers the penis and the pouch encloses the scrotum and the base of the penis. A first elastic band extends around and is attached to the sheath. The first elastic band is positioned at a juncture of the pouch portion and the cylindrical portion. Blood flow through the penis is restricted by the first elastic band.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
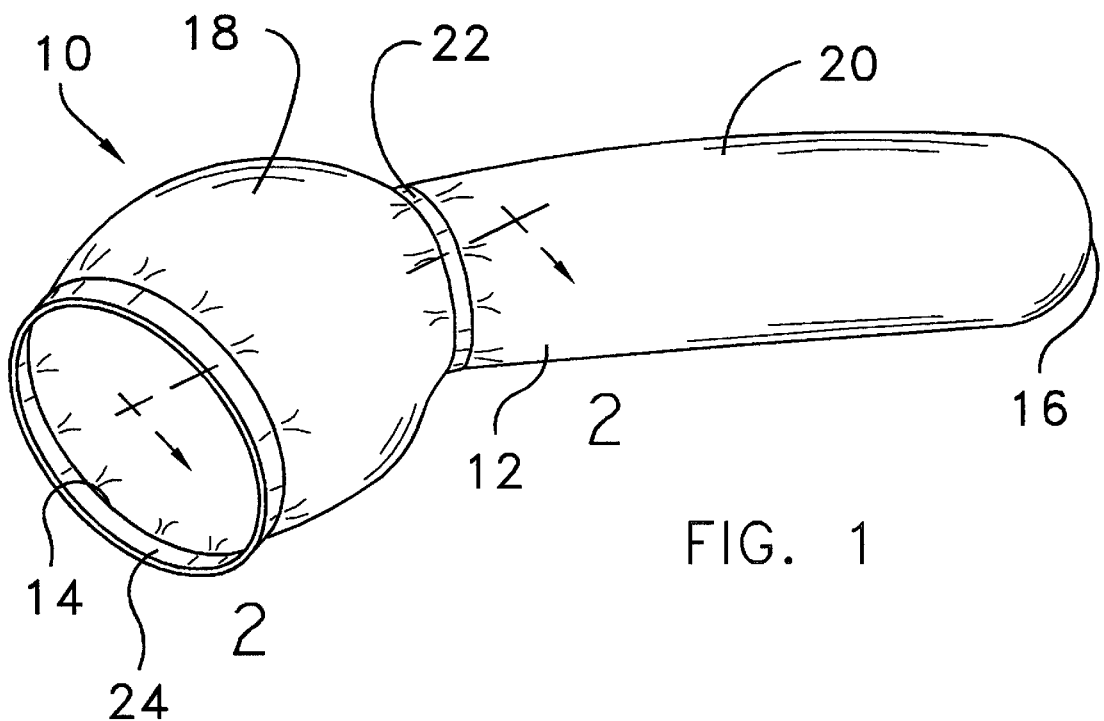
FIG. 1 is a schematic perspective view of a new condom device according to the present invention.
Figure 2:
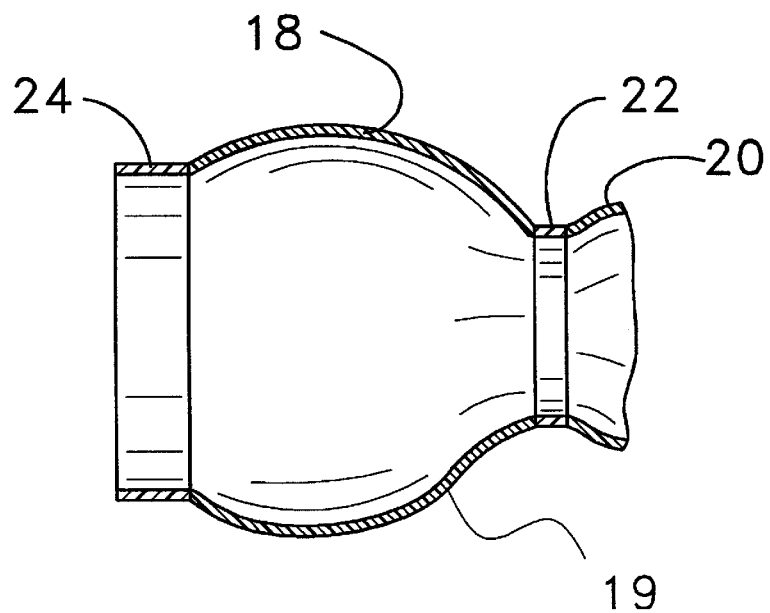
FIG. 2 is a schematic cross-sectional view taken along line 2—2 of the present invention.

With reference now to the drawings, and in particular to FIGS. 1 and 2 thereof, a new condom device embodying the principles and concepts of the present invention and generally designated by the reference numeral 10 will be described.

As best illustrated in FIGS. 1 and 2, the condom device 10 generally comprises a single and continuous sheath 12 of thin walled tubular construction having an open first end 14 and a closed second end 16. The sheath 12 includes a pouch portion 18 abutting the first end 14 and a cylindrical portion 20 abutting the second end 16. The device 10 is positioned over male genitalia such that the cylindrical portion 20 covers the penis and the pouch portion 18 encloses the scrotum and the base of the penis. The pouch portion 18 has a diameter generally more than twice a diameter of the cylindrical portion 20. The sheath 12 comprises an elastomeric material.

A first elastic band 22 extends around and is integrally attached to the sheath. The first elastic band 22 is positioned at a juncture of the pouch portion 18 and the cylindrical portion 20. A second elastic band 24 is integrally attached to and extends along a length of the first end 14. Blood flow through the penis is restricted by the elastic bands 22, 24.

In use, the device 10 is used as a conventional condom. The elastic bands 22, 24 restrict flow of blood through the penis which desensitizes the penis during sexual intercourse.

As best illustrated in FIGS. 1 and 2, the condom device 10 generally comprises a single and continuous sheath 12 of thin walled tubular construction having an open first end 14 and a closed second end 16. The sheath 12 includes a pouch portion 18 abutting the first end 14 and a cylindrical portion 20 abutting the second end 16. The pouch portion has a perimeter wall 19 extending between a juncture between the pouch 18 and cylindrical 20 portions and the first end of the sheath. The perimeter wall 19 has a generally bell-shaped cross section (see FIG. 2) in a plane extending along a longitudinal axis of the sheath. The device 10 is positioned over male genitalia such that the cylindrical portion 20 covers the penis and the pouch portion 18 encloses the scrotum and the base of the penis. The pouch portion 18 has a diameter generally more than twice a diameter of the cylindrical portion 20. The sheath 12 comprises an elastomeric material.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A prophylactic and desensitizing condom device comprising:

a single and continuous sheath of thin walled tubular construction having an open first end and a closed second end, said sheath including a pouch portion adjacent said first end and a cylindrical portion adjacent said second end such that when said device is positioned over male genitalia said cylindrical portion covers the penis and said pouch portion encloses the scrotum and the base of the penis, said cylindrical portion having a substantially uniform diameter along a length of said cylindrical portion from said second end of said sheath toward said pouch portion;

a first elastic band extending around and being integrally attached to said sheath, said first elastic band being positioned at a juncture of said pouch portion and said cylindrical portion, said first elastic band constricting and reducing a diameter of an inner surface of said sheathe such that a diameter of said cylindrical portion is reduced from said substantially uniform diameter at the juncture between said cylindrical portion and said pouch portion;

wherein blood flow through the penis is restricted by said first elastic band;

wherein said pouch portion has a diameter generally more than twice a diameter of said cylindrical portion;

wherein said sheath comprises an elastomeric material;

a second elastic band being integrally attached to and extending along a length of said first end, said first elastic band and said second elastic band each having a common central axis;

wherein said pouch portion has a perimeter wall extending between said juncture and said first end of said sheath, said perimeter wall having a generally bell-shaped cross section in a plane extending along a longitudinal axis of said sheath; and wherein said first elastic band has a first diameter and said second elastic band has a second diameter, said first diameter being approximately 60 percent of said second diameter.

* * * * *